US006673566B1

(12) United States Patent
Waters et al.

(10) Patent No.: US 6,673,566 B1
(45) Date of Patent: Jan. 6, 2004

(54) DIAGNOSIS OF PATHOGEN INFECTIONS THROUGH ANALYSIS OF NITRITE PRODUCTION BY ANTIGEN STIMULATED LEUKOCYTES

(75) Inventors: Wade R. Waters, Stratford, IA (US); Mitchell V. Palmer, Nevada, IA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 196 days.

(21) Appl. No.: 10/044,631

(22) Filed: Jan. 10, 2002

(51) Int. Cl.[7] .................................................. C12N 5/00
(52) U.S. Cl. ............................ 435/27; 435/29; 435/383
(58) Field of Search ............................. 435/27, 29, 383

(56) References Cited

U.S. PATENT DOCUMENTS

| | | | | |
|---|---|---|---|---|
| 3,634,198 | A | * | 1/1972 | Truhan |
| 4,631,255 | A | * | 12/1986 | Takino et al. |
| 5,910,421 | A | * | 6/1999 | Small, Jr. et al. |
| 6,326,357 | B1 | | 12/2001 | Phillips et al. |

* cited by examiner

*Primary Examiner*—Leon B. Lankford, Jr.
(74) *Attorney, Agent, or Firm*—John D. Fado; Randall E. Deck

(57) ABSTRACT

Peripheral blood mononuclear cells which have been isolated from an animal that is infected with a microbial pathogen produce nitric oxide in response to stimulation with antigens from that pathogen. Determination of nitric oxide production in cultures of peripheral blood mononuclear cells stimulated with a pathogen's antigens may thus provide an indication of infection of the animal.

13 Claims, 2 Drawing Sheets

DIAGNOSIS OF PATHOGEN INFECTIONS THROUGH ANALYSIS OF NITRITE PRODUCTION BY ANTIGEN STIMULATED LEUKOCYTES

BACKGROUND OF THE INVENTION

1. Field of the Invention

The invention relates to a novel method for detecting tuberculosis and other infections in animals.

2. Description of the Prior Art

Cell-mediated immune responses are critical in the host defense against intracellular bacterial pathogens (Chan and Kaufmann, 1994, Immune mechanisms of protection, In Tuberculosis: Pathogenesis, protection, and control, B. R. Bloom, (ed.), American Society of Microbiology, Washington, D.C., pp. 389–415; Cheville et al., 1993, "Immune responses and protection against infection and abortion in cattle experimentally vaccinated with mutant strains of Brucella abortus," American Journal of Veterinary Research 54:1,591–1,597; Chiodini, 1996. Immunology: Resistance to paratuberculosis, Veterinary Clinics of North America 12:313–342). A key component of this response is the clonal expansion of lymphocytes and the elaboration of cytokines that activate macrophages for the killing of bacteria located within the phagosomal compartment. Potent mediators of intra-phagosomal killing are reactive nitrogen intermediates (e.g., nitric oxide, NO) produced via the induction of inducible NO synthase (NOS), often as a sequalae to IFN-γ, TNF-α, or LPS stimulation (MacMicking et al., 1997, "Nitric oxide and macrophage function", Annual Reviews of Immunology, 15:323–350; Kaufmann, 1999, "Cell-mediated immunity: Dealing a direct blow to pathogens", Current Biology, 9:R97–99).

SUMMARY OF THE INVENTION

We have now discovered that peripheral blood mononuclear cells which have been isolated from an animal that is infected with a microbial pathogen produce nitric oxide in response to stimulation with antigens from that pathogen. Determination of nitric oxide production in cultures of peripheral blood mononuclear cells stimulated with a microbial pathogen's antigens may thus provide a specific indication of infection of the animal by that pathogen.

In accordance with this discovery, it is an object of this invention to provide an improved method for detecting an infection in an animal by a pathogenic microorganism.

Another object of this invention is to provide a method for detecting an infection in an animal which is specific for a particular microbial pathogen.

Yet another object of the invention is to provide a method for detecting Mycobacterium or Brucella infections in an animal.

Other objects and advantages of this invention will become readily apparent from the ensuing description.

DETAILED DESCRIPTION OF THE INVENTION

Figure 1:
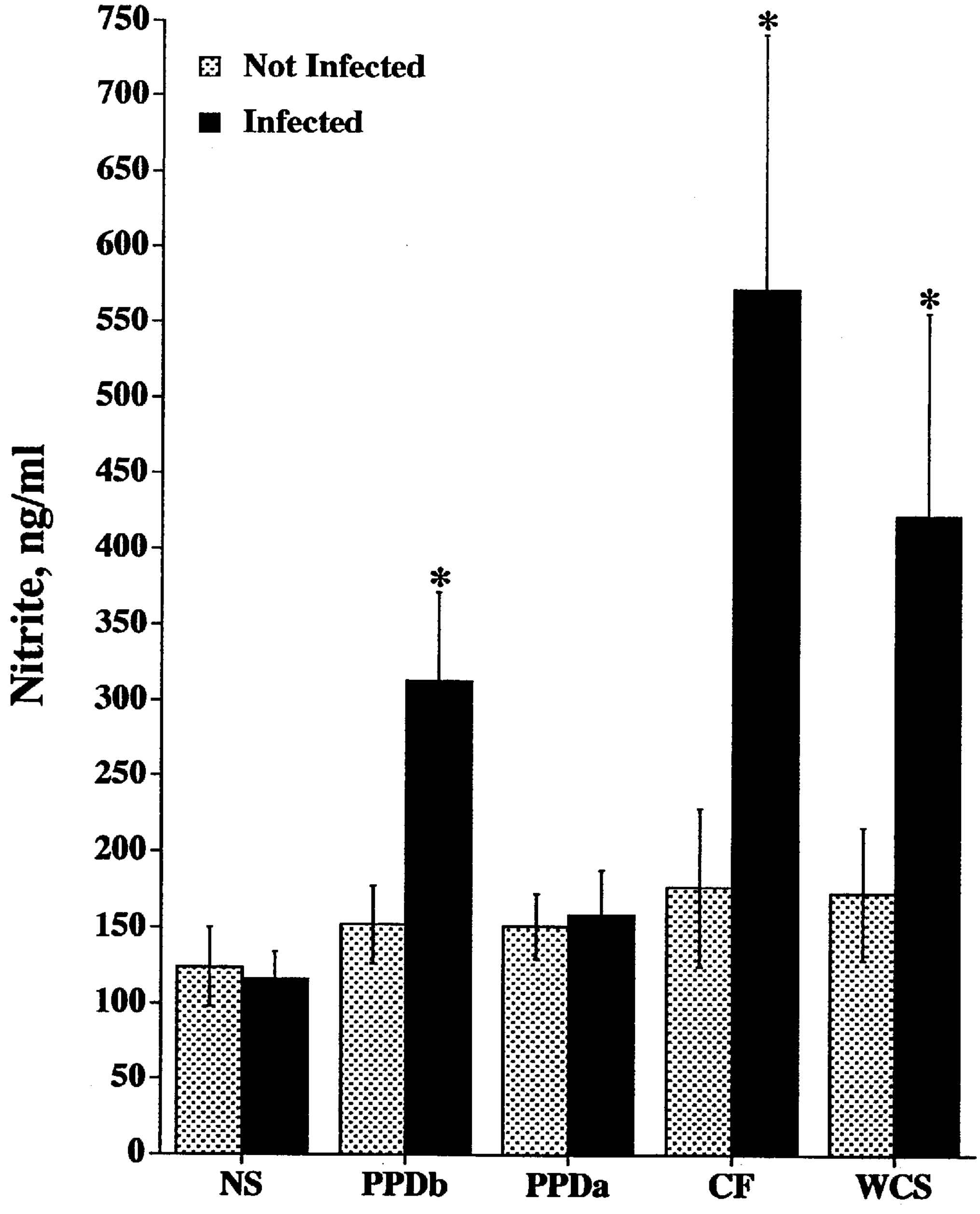
FIG. 1 shows the antigen-specific induction of nitrite production by PBMC from *Mycobacterium bovis*-infected white-tailed deer. Dotted bars indicate responses from non-infected deer (n=13 for NS, PPDb, and PPDa and n=10 for CF and WCS). Closed bars indicate responses of *M. bovis*-infected deer (n=12 NS, PPDb, and PPDa and n=5 for CF and WCS). [*Differ (P<0.05) from responses of deer not infected with *M. bovis*].

The method of this invention is effective for specifically detecting infections in an immunologically competent or mature animal by pathogenic microorganisms which elicit a cell-mediated immune response therein. The invention is particularly applicable for the detection of infections in mammals, including, but not limited to cervine, bovine, equine, porcine, ovine, caprine, and primates. In a particularly preferred embodiment, the method is used for detecting infections in ruminants and livestock, including cattle, sheep, goats, and swine, wildlife such as antelope, deer, elk, and bison, and humans. It is also envisioned that the method may be used for detecting infections caused by any microbial pathogen which elicits a cell-mediated immune response in the animal, and hence may be used for detecting infections by bacterial and protozoan pathogens. However, the method is preferably used for detecting infections by Mycobacterium species, particularly *M. bovis, M. tuberculosis, M. africanum* and *M. avium* subspecies paratuberculosis, Brucella species, particularly *B. abortus, B. suis, B. melitensis, B. ovis*, and *B. canis*, and protozoan pathogens such as Leishmania and Babesia species.

In summary, the detection of an infection in an animal by a pathogenic microorganism in this invention includes the steps of:

a) providing a sample of peripheral blood mononuclear cells (PBMC) from a test animal;

b) culturing the PBMC in a culture medium containing an antigen for the suspected pathogenic microorganism; and c) determining the presence of nitric oxide produced by the culture of the PBMC in b).

The determination of nitric oxide production by the PBMC culture is an indication of the presence of an infection in the animal by the suspected pathogen.

The sample of the PBMC for use in the culture may be isolated PBMC (i.e., separated from red blood cells) or provided as whole blood, although the use of the latter may preclude the use of certain nitric oxide assays, such as calorimetric assays.

Following their recovery from the animal to be tested, the PBMC are exposed in a culture media in vitro to an antigen from the suspected microbial pathogen in an amount and incubated under conditions and for a period of time effective to stimulate or activate the cells to division or blastogenesis. Techniques for in vitro lymphocyte activation which may also be used herein are well known in the art, and include those described by Weiler and Von Bulow (1987, Vet. Immunol. Immunopathol., 14:257–267) and Stites [Clinical Laboratory Methods for Detection of Cellular Immune Function, In: *Basic & Clinical Immunology*, fifth edition, Stites et al. (ed.), Lange Medical, Los Altos, Calif., (1984), pp. 362–365], the contents of each of which are incorporated by reference herein.

In brief, separated PBMC are suspended in a suitable tissue culture medium with added antigen and incubated, preferably at about 37° C. in a $CO_2$ containing atmosphere, for approximately 48 to 72 hrs. The particular culture medium selected is not critical and a variety of tissue culture media may be used. However, without being limited thereto, culture is preferably conducted in RPMI medium supplemented with sera (FBS). The amount of antigen added to the media may be readily determined, and will vary with the particular antigen selected and the cell concentration. Alternatively, techniques for the culture of PBMC in whole blood samples which may also be used herein are described by Rothel et al. (1990, Austr. Vet. J., 67:134–137), Wood et al. (1992, Vet. Microbiol., 31:71–79), and Whipple et al. [2001, J. Vet. Diag. invest., 13(2):117–122], the contents of each of which are incorporated by reference herein.

The antigens used in the culture should be antigens derived from the suspected microbial pathogen, and should be effective for eliciting a cell-mediated immune response in the subject animal. Where a high level of specificity is desired, the antigen should not cross react with other species. Numerous antigens specific for a wide variety of pathogens are known in the art and are suitable for use herein. In a first preferred embodiment for the detection of *Mycobacterium bovis, M. tuberculosis*, or *M. africanum*, preferred specific antigens include, but are not limited to *M. bovis* or *M. tuberculosis* purified protein derivatives (PPDs) such as described by Angus (1978, Production of Reference PPD tuberculins for Veterinary Use in the United States, J. Biological Standards, 6:221–227) and the USDA (1999, Bovine tuberculosis eradication: Uniform Methods and Rules, effective Jan. 22, 1999, USDA/APHIS Veterinary Service, U.S. Government Printing Office, Washington, D.C., APHIS publication no. 91-45-011), as well as ESAT-6 and MPT64 described by Buddle et al., (1999, Differentiation between Mycobacterium bovis BCG-vaccinated and *M. bovis*-infected cattle by using recombinant mycobacterial antigens, Clin. Diagn. Lab. Immunol., 6:1–5); Elhay et al., (1998, Delayed-type hypersensitivity responses to ESAT-6 and MPT64 from Mycobacterium tuberculosis in the guinea pig, Infect. Immun., 66:3454–6); Pollock et al. (1997, The potential of the ESAT-6 antigen secreted by virulent mycobacteria for specific diagnosis of tuberculosis, J. Infect. Dis., 175:1251–4); and van Pinxteren et al., (2000, Diagnosis of tuberculosis based on the two specific antigens ESAT-6 and CFP10, Clin. Diagn. Lab. Immunol., 7:155–160). These antigens are specific for *M. bovis* and *M. tuberculosis* and do not exhibit a high level of cross-reactivity with Mycobacterium avium. Suitable antigens for the detection of *M. avium* subspecies paratuberculosis include those described by Harris (2001, *Mycobacterium avium* subspecies paratuberculosis, Vet. Medicine Clinical Reviews, 14:489–512) and McDonald et al. (1999, Evaluation of diagnostic tests of Johne's disease in young cattle, Australian Vet. J., 77:113–119). The contents of all of these above-mentioned references are incorporated by reference herein. For detection of Brucella species, use of irradiated bacteria or other known conventional antigens is preferred.

Nitric oxide production by the PBMC cultures may be determined using a variety of techniques, and numerous conventional assays have been described for measurement of nitric oxide in biological fluids which are suitable for use herein. Moreover, the production of nitric oxide may be determined directly or indirectly, that is, nitric oxide per se may be measured, or nitric oxide may be determined by measurement of nitric oxide breakdown products such as nitrite. For example, without being limited thereto, conventional methods of measuring the concentration of NO include HPLC, spectrophotometry, chemiluminescence, electrochemical analysis and electron paramagnetic resonance (EPR). These and other methods of detecting nitric oxide are fully described by Feelisch and Stanler (ed.) (in Methods in Nitric Oxide Research, 1996), Allen et al. (U.S. Pat. No. 6,287,452), Stamler (U.S. Pat. No. 5,459,076), and Lai (U.S. Pat. No. 6,306,609), the contents of each of which is incorporated by reference herein. These techniques may be used herein for detecting NO production by cultures of either isolated PBMC or PBMC in whole blood. However, in the preferred embodiment, the PBMC are separated from the buffy coat of whole blood prior to culture and NO production is determined by detection of nitrite calorimetrically using the Griess reaction as described in detail in the Examples. Nitrite is the stable oxidation product of NO and the amount of nitrite within culture supernatants is indicative of the amount of NO produced by cells in culture.

Regardless of the measurement technique used, the NO levels measured in the test cultures may be compared to negative controls (no antigen in the culture) and, optionally, with cultures incubated with other closely related species. Production of NO levels substantially greater (statistically significant) than the controls is an indication of infection in the test animal by the suspected microbial pathogen.

The following example is intended only to further illustrate the invention and is not intended to limit the scope of the invention which is defined by the claims.

EXAMPLE 1

MATERIALS AND METHODS

Experimental Animals and *M. bovis* Challenge

White-tailed deer (1–1.5 years of age) used for the study were either born at the National Animal Disease Center (NADC; Ames, Iowa, USA) and raised within our tuberculosis-free herd or obtained from producers of farmed white-tailed deer with no history of tuberculosis in their herds. Five castrated males and seven non-pregnant females were experimentally infected with *M. bovis* as described (Palmer et al., 1999, Development of a model of natural infection with *Mycobacterium bovis* in white-tailed deer, Journal of Wildlife Diseases, 35:450–457) and 11 castrated males and two non-pregnant females served as non-infected controls. The strain of *M. bovis* used for the challenge inoculum (strain 1315) was isolated from a white-tailed deer from Michigan in 1994 (Schmitt et al., 1997, Bovine tuberculosis in free-ranging white-tailed deer from Michigan, Journal of Wildlife Diseases, 33:749–58). The challenge inoculum consisted of 300 colony forming units (cfu) of mid-log-phase *M. bovis* grown in Middlebrook's 7H9 media supplemented with 10% oleic acid-albumin-dextrose complex (OADC, Difco, Detroit, Mich., USA) plus 0.05% Tween 80 (Sigma Chemical Co., St. Louis, Mo., USA) as described (Bolin et al., 1997, Infection of swine with *Mycobacterium bovis* as a model of human tuberculosis, Journal of Infectious Diseases, 176:1559–1566). To harvest tubercle bacilli from the culture media, cells were pelleted by centrifugation at 750×G, washed twice with 1 ml of phosphate-buffered saline solution (PBS, 0.01 M, pH 7.2), and diluted to the appropriate cell density in 2 ml of PBS. Enumeration of bacilli was by serial dilution plate counting on Middlebrook's 7H11 selective media (Becton Dickinson, Cockeysville, Md., USA). For intratonsilar inoculation, deer were restrained and anesthetized with ketamine (6 mg/kg, Fort Dodge Animal Health, Fort Dodge, Iowa, USA) and xylazine (2 mg/kg, Bayer Corp., Shawnee Mission, Kans., USA) given intramuscularly. Effects of xylazine were reversed by intravenous administration of 4 mg/kg tolazoline (Lloyd Laboratories, Shenandoah, Iowa, USA). The challenge inoculum was instilled directly into the tonsilar crypts of anesthetized deer. Infected deer were housed in pens (two-four deer/pen) inside a biosecurity level 3 building with negative air-flow exiting the building through high efficiency particulate air filters. Three of the 13 non-infected deer were housed similarly as infected deer in a separate building with the remainder of the non-infected deer housed in a paddock of ~2 hectare. Deer were fed a pelletized ration and alfalfa hay.

Prior to the experiment and 90 days after inoculation, experimentally inoculated deer and three of the control deer were tested for immune reactivity to mycobacterial antigens by the comparative cervical skin test as described (Palmer et al., 1999, ibid). Results were used to categorize deer as negative, suspect, or reactor in relation to exposure to *M. bovis* (United States Department of Agriculture, 1999, Bovine tuberculosis eradication uniform methods and rules, APHIS 91-45-011, U.S. Government Printing Office, Washington D.C. 34 pages). All *M. bovis*-inoculated deer were euthanized at various time points ranging from 6–11 month post inoculation by intravenous injection of sodium pentobarbital (Fort Dodge Laboratories). Mononuclear cell culture and antigens Mononuclear cells were isolated from buffy coat fractions of peripheral blood collected in acid citrate dextrose using standard procedures (Burton and Kehrli, 1996, Effects of dexamethasone on bovine circulating T lymphocyte populations, Journal of Leukocyte Biology, 59:90–99). Wells of 96-well round-bottomed microtiter plates (Falcon, Becton-Dickinson, Lincoln Park, N.J., USA) were seeded with $2\times10^5$ mononuclear cells in a total volume of 200 μl per well. The medium was RPMI 1640 (Gibco, Invitrogen Life Technologies, Frederick, Md., USA) supplemented with 25 mM HEPES buffer, 100 units/ml penicillin, 0.1 mg/ml streptomycin, $5\times10^{-5}$M 2-mercaptoethanol (Sigma Chemical Co., St. Louis, Mo., USA), and 10% fetal bovine sera (FBS). Wells contained medium plus 5 μg/ml *M. bovis* purified protein derivative (PPDb; CSL Limited, Parkville, Victoria, Australia), 5 μg/ml *M. avium* purified protein derivative (PPDa; CSL Limited), 5 μg/ml *M. bovis* strain 1315 culture filtrate (CF), 10 μg/ml *M. bovis* strain 1315 whole cell sonicate (WCS), 20 μg/ml *M. bovis* strain 1315 proteinase K digested whole cell sonicate (PK), or medium alone (no stimulation). The CF was from 2 wk *M. bovis* strain 1315 cultures (bacteria pelleted, supernatant harvested and filtered (0.22 μm) twice). For the WCS antigen preparation, 2 wk *M. bovis* strain 1315 cultures in Middlebrook's 7H9 media supplemented with 10% OADC were pelleted, sonicated in PBS, and further disrupted with 0.1–0.15 mm glass beads (Biospec Products, Bartlesville, Okla., USA) in a bead beater (Biospec Products) then placed on ice. The preparation was then centrifuged and the supernatant harvested, filtered (0.22 μm), and stored at −20° C. The PK antigen was prepared by digestion of the WCS in a 1 mg/ml proteinase K (Roche Molecular Biochemicals, Indianapolis, Ind., USA) solution (50 mM Tris, 1 mM $CaCl_2$ buffer, pH 8.0) for 1 hr. at 50° C. Protein concentrations of the CF, WCS, and PK antigens were determined using a protein determination kit (Bio Rad, Hercules, Calif., USA). Mononuclear cell cultures were incubated for 24, 48, or 72 hr. at 37° C. in 5% $CO_2$ in air. Supernatants were removed from the cell pellet and stored at −70° C. for later analysis.

Monocytes were isolated from buffy coat fractions of peripheral blood of non-infected deer by adherence in 25 $cm^2$ flasks at 37° C. for 1 hr. Cells were cultured for 2 wk at 37° C. with 5% $CO_2$ in RPMI 1640 (Gibco, Invitrogen Life Technologies, Frederick, Md., USA) supplemented with L-glutamine, penicillin, streptomycin, 2-ME, 10% heat-inactivated fetal calf serum, and 10% heat-inactivated white-tailed deer serum. Medium was changed every 3–4 days during the culture period. At the end of the 2 wk culture period, cells were stimulated for 24 hr. with or without 1 μg/ml Mannheimia haemolytica LPS (Brogden et al., 1995, *Pasteurella haemolytica* lipopolysaccharide-associated protein induces pulmonary inflammation after bronchoscopic deposition in calves and sheep, Infection and Immunity, 63:3595–3599). Supernatants were harvested and stored at −70° C. for later analysis.

Nitric Oxide Assay

Nitrite is the stable oxidation product of NO and the amount of nitrite within culture supernatants is indicative of the amount of NO produced by cells in culture. Nitrite was measured using the Griess reaction (Rajaraman et al., 1998, Effect of vitamins A and E on nitric oxide production by blood mononuclear leukocytes from neonatal calves fed milk replacer, Journal of Dairy Science, 81:3,278–3,285) performed in 96-well microtiter plates (Immunolon 2, Dynatech Laboratories, Inc., Chantilly, Va., USA). Culture supernatant (100 μl) was mixed with 100 μl of Griess reagent (0.5% sulfanilamide [Sigma Chemical Co.] in 2.5% phosphoric acid [Mallinckrodt Chemicals, Inc., Paris, Ky., USA]) and 0.05% N-(1-naphthyl) ethylenediamine dihydrochloride (Sigma Chemical Co.). The mixture was incubated at 21° C. for 10 minutes. Absorbencies of test and standard samples at 550 nm were measured using an automated ELISA plate reader (Molecular Devices, Menlo Park, Calif., USA). Dilutions of standards were made using supplemented RPMI 1640 media. Absorbencies of standards, controls, and test samples were converted to ng/ml of nitrite by comparison with absorbencies of sodium nitrite (Fisher Chemicals, Fair Lawn, N.J., USA) standards within a linear curve fit. $N^G$-monomethyl-L-arginine (L-NMMA; Calbiochem, La Jolla, Calif., USA), a competitive inhibitor of the enzyme nitric oxide synthase (NOS) (1.15 mM; equimolar to the amount of L-arginine in the culture medium) was added to parallel cultures to verify that the nitrite produced was due to the activity of NOS.

Statistics

Data were analyzed by one-way analysis of variance followed by Tukey-Kramer multiple comparisons test. Differences between groups were considered significant if probability values of $P<0.05$ were obtained.

RESULTS

All *M. bovis*-inoculated deer were classified as negative by the comparative cervical test of delayed type hypersensitivity prior to exposure and as reactors 90 days post inoculation. All non-infected deer tested by the comparative cervical test were classified as negative for skin hypersensitivity to *M. bovis*.

White-tailed deer macrophages produced nitrite in response to stimulation with 1 μg/ml *M. haemolytica* LPS (Table 1). The response to LPS was significantly ($P<0.05$) higher (87+/−14 ng/ml nitrite) than the response of non-stimulated cells (47+/−8 ng/ml nitrite). Nitrite levels detected in culture supernatants of cells stimulated with LPS in the presence of L-NMMA did not differ ($P>0.05$) from nitrite levels in supernatants of the non-stimulated cultures.

Figure 2:
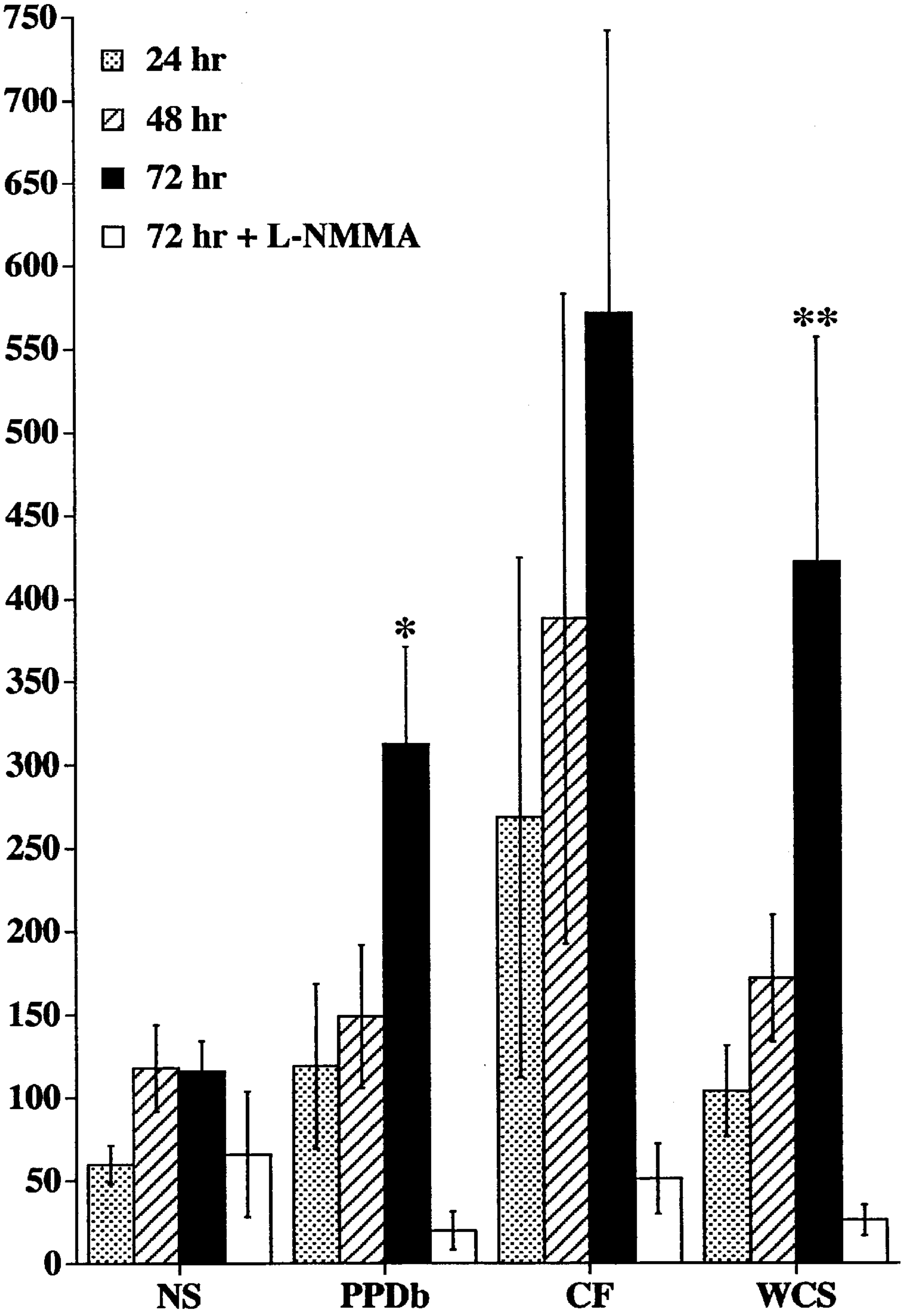
FIG. 2 shows the antigen-specific production of nitrite by PBMC from *M. bovis*-infected white-tailed deer is cumulative over time in culture and inhibited by presence of a nitric oxide synthase inhibitor (L-NMMA). Dotted bars represent responses at 24 hr. (n=5), hatched bars represent responses at 48 hr. (n=5), closed bars represent responses at 72 hr. (n=5 for CF and WCS, n=12 for NS and PPDb), and open bars represent responses at 72 hr. plus L-NMMA (n=5 for CF and WCS, n=12 for NS and PPDb). [P<0.05, ** P<0.01, differs when compared to responses at 24 hr., 48 hr., or 72 hr. plus L-NMMA].

Nitrite production by PBMC from infected deer in response to stimulation with *M. bovis* antigens exceeded ($P<0.05$) that of the response of non-infected deer to the respective antigen (FIG. 1). The response to *M. bovis* antigens by PBMC from *M. bovis*-infected deer exceeded ($P<0.05$) the response of parallel cultures receiving no stimulation. Antigens produced from *M. bovis* strain 1315 (i.e., CF and WCS) tended ($P<0.1$) to generate a greater response than did non-homologous *M. bovis* antigens (i.e., PPDb). The response of infected deer to *M. bovis* antigens PPDb, CF, and WCS exceeded ($P<0.05$) the response to stimulation with antigens prepared from a related species of mycobacteria, *M. avium* PPD (i.e., PPDa). Nitrite production by PBMC from infected deer in response to stimulation with *M. bovis* antigens was cumulative over time in culture with responses increasing from 24–72 hrs. in culture (FIG. 2). Nitrite accumulation within PPDb- and WCS-stimulated cultures incubated for 72 hr. exceeded ($p<0.05$) that of parallel cultures incubated for either 24 or 48 hrs. with PPDb or WCS, respectively. Addition of L-NMMA ablated this response, indicating that nitrite accumulation within the supernatants results from the activity of NOS (FIG. 2). Stimulation of PBMC from infected deer with a proteinase K-digested *M. bovis* WCS antigen for 72 hr. did not induce a significant response (138±48.0 for the proteinase K-digested *M. bovis* WCS stimulation versus 116±18.2 for no stimulation).

DISCUSSION

Mononuclear cells isolated from *M. bovis*-infected deer produced NO in response to *M. bovis* but not *M. avium* antigens, indicating antigen-specificity. This response required intact M. bovis proteins because proteinase K-digestion of the *M. bovis* WCS abrogated significant nitrite production as detected with intact WCS. The proteinase K-digested *M. bovis* WCS antigen does react, however, with antibodies in serum obtained from *M. bovis*-infected deer by western blot analysis and ELISA (data not shown). Thus, B cells from infected deer respond to non-proteinaceous antigens or peptides by production of antibody specific to these antigens whereas the cellular response, as detected by NO production, requires intact proteins. It is likely that protein antigens (e.g., *M. bovis* WCS antigens) presented to T cells results in elaboration of cytokines such as TNF-α and/or IFN-γ that in turn induce NO production by macrophages.

In summary, mononuclear cells isolated from *M. bovis*-infected deer produce NO in response to stimulation with *M. bovis* but not *M. avium* antigens. The response was dependent upon intact *M. bovis* proteins. The response was also abrogated by addition of NOS inhibitor, L-NMMA.

TABLE 1

Nitrite (ng/ml) detected in culture supernatants of white-tailed deer adherent peripheral blood mononuclear cells stimulated with *Mannheimia haemolytica* LPS

| Animal | 536 | 542 | 564 | 568 | 540 | 548 | Mean | SEM |
|---|---|---|---|---|---|---|---|---|
| Medium | 57 | 13 | 38 | 63 | 69 | 44 | 47 | 8 |
| LPS | 126 | 25 | 88 | 114 | 88 | 82 | 87* | 14 |
| LPS + L-NMMA | 25 | 19 | 19 | 25 | 38 | 57 | 30 | 6 |

*$P < 0.05$, mean response to LPS differs from mean responses to no stimulation (i.e., medium) or stimulation with LPS + L-NMMA.

It is understood that the foregoing detailed description is given merely by way of illustration and that modifications and variations may be made therein without departing from the spirit and scope of the invention.

We claim:

1. A method for detecting an infection in an animal by a pathogenic microorganism which elicits a cell-mediated immune response comprising:

a) providing a sample of peripheral blood mononuclear cells from a test animal;

b) culturing said peripheral blood mononuclear cells in a culture medium containing an antigen for a suspect pathogenic microorganism (incubating under conditions and for a period of time effective to stimulate said cells); and c) determining the presence of nitric oxide produced by the culture of said peripheral blood mononuclear cells in b), wherein the determination of nitric oxide production is an indication of the presence of an infection in said animal by said suspect pathogenic microorganism.

2. The method of claim 1 wherein said animal is a mammal.

3. The method of claim 1 wherein said animal is selected from the group consisting of cervine, bovine, equine, porcine, ovine, caprine, and primates.

4. The method of claim 1 wherein said mammal is a ruminant.

5. The method of claim 1 wherein said animal is selected from the group consisting of cattle, sheep, goats, swine, antelope, deer, elk, and bison.

6. The method of claim 1 wherein said sample of peripheral blood mononuclear cells is substantially free of red blood cells.

7. The method of claim 1 wherein said sample of peripheral blood mononuclear cells comprises whole blood.

8. The method of claim 1 wherein said pathogenic microorganism is selected from the group consisting of Mycobacterium species and Brucella species.

9. The method of claim 8 wherein said pathogenic microorganism is a Mycobacterium species.

10. The method of claim 9 wherein said Mycobacterium species is selected from the group consisting of *M. bovis, M. tuberculosis, M. africanum*, and *M. avium* subspecies paratuberculosis.

11. The method of claim 8 wherein said Brucella species is selected from the group consisting of *B. abortus, B. suis, B. melitensis, B. ovis*, and *B. canis.*

12. The method of claim 1 wherein said determination of nitric oxide production comprises measuring nitric oxide in the culture of said peripheral blood mononuclear cells.

13. The method of claim 1 wherein said determination of nitric oxide production comprises measuring nitrite in the culture of said peripheral blood mononuclear cells.

* * * * *